United States Patent [19]
Briend et al.

[11] Patent Number: 6,051,241
[45] Date of Patent: Apr. 18, 2000

[54] NITROGEN MONOXIDE COMPOSITION FOR USE AS A DRUG

[75] Inventors: Robert Briend, Les-Clayes-sous-Bois; Marie-Hélène Renaudin, Paris, both of France

[73] Assignee: L'Air Liquide, Societe Anonyme pour L'Etude et L'Exploitation des Procedes Georges Claude, Paris, France

[21] Appl. No.: 09/051,641

[22] PCT Filed: Oct. 17, 1996

[86] PCT No.: PCT/FR96/01624

§ 371 Date: Aug. 10, 1998

§ 102(e) Date: Aug. 10, 1998

[87] PCT Pub. No.: WO97/15312

PCT Pub. Date: May 1, 1997

[30] Foreign Application Priority Data

Oct. 20, 1995 [FR] France ................... 95/12345

[51] Int. Cl.$^7$ ...................... A61K 9/00

[52] U.S. Cl. ............ 424/400; 424/422; 424/423
[58] Field of Search ................ 424/400, 93.3, 424/93.48, 61, 71

[56] References Cited

U.S. PATENT DOCUMENTS 5,443,826  8/1995  Borody ................ 424/93.3

FOREIGN PATENT DOCUMENTS

| 92/10228 | 6/1992 | WIPO . |
| 94/00180 | 1/1994 | WIPO . |
| 94/22499 | 10/1994 | WIPO . |

*Primary Examiner*—Thurman K. Page
*Assistant Examiner*—William E. Benston, Jr.
*Attorney, Agent, or Firm*—Burns, Doane, Swecker & Mathis, L.L.P.

[57] ABSTRACT

The invention relates to a method for the treatment or prevention of hypoperfusions of abdominal organs comprising administering a gaseous medication containing nitrogen monoxide and carbon dioxide to the patient. The gaseous medication is administered by the intra-abdominal route.

5 Claims, No Drawings

NITROGEN MONOXIDE COMPOSITION FOR USE AS A DRUG

This invention relates to the use of a stable gaseous compound on a base of nitrogen monoxide (NO) and carbon dioxide ($CO_2$) to produce a gaseous medication intended for the treatment or prevention, by the intra-abdominal route, of hypoperfusion of the abdominal organs, in particular, in the case of a procedure involving laparoscopy or laparosurgery.

Nitrogen monoxide is produced naturally in mammals by an enzyme, called NO-synthase, which is expressed in terms of its makeup by the endothelial cells, by the platelets, and by the central and peripheral nervous systems. Another form of calcium-independent NO-synthase can be induced by different stimuli (especially liposaccharides) in numerous cells, such as macrophages, lymphocytes, myocardial cells, endothelial cells, and the smooth muscular cells.

Nitrogen monoxide is an important biological messenger in mammals, and this molecule plays a decisive role in the local control of hemodynamics.

It has been possible to make evident the release of NO by means of the endothelial cells in the case of variations in the blood flow. Nitrogen monoxide appears especially as a major component of the physiological adaptation of the vascular diameter to blood perfusion: reactive hyperemia is thus attenuated in a most noticeable fashion on the coronary level. Conversely, a chronic increase in the blood flow, produced by an arteriovenous fistula, increases the dependent relaxations of the endothelium.

The capacity of nitrogen monoxide, produced at the level of the vascular wall and in the neighboring tissues, to regulate precisely the vascular tonus by adaptation of the blood flow is remarkable. Likewise, it has been assumed that the NO that is released during neuronal activity could regulate the tonus of cerebral microcirculation, thus linking the activity and the cerebral blood flow. We also recall the role played by NO in the regulation of the proliferation of smooth vascular muscle which is a decisive factor in vascular compliance.

Nitrogen monoxide furthermore controls the post-capillar venular permeability.

Nitrogen monoxide also participates in hormonal regulation mechanisms at the level of the kidney by inhibiting the release of renin, and on the cardiovascular level by opposing the release of the natriuretic factor (ANF).

Finally, in vivo, platelet activation is under the permanent control of endothelial nitrogen monoxide and, to a lesser degree, it is under the control of platelet NO-synthase itself. During aggregation, the platelets release nucleotides (ATP, ADP), serotonin, PAF, thromboxane A2, and vasopressin; they can also initiate the gush of coagulation by releasing thrombin. In response to ATP, ADP, serotonin, PAF, and thrombin, the endothelial cells release NO and prostacyclin, both of which act together to prevent and counter the process of platelet aggregation.

The abnormal decline in the nitrogen monoxide rate, observed in the case of numerous diseases, seems to confirm the importance of its role in the organism. Such a decline is characteristic of hypertension, hypercholesterolemia, atherosclerosis, and diabetes.

Likewise, a very early reduction of the basal release of NO would be the cause of problems related to the re-perfusion of ischemic areas, such as coronary thrombosis and vasospasms.

Various vasodilator agents have been developed so far on the basis of these findings. These substances, known as nitrovasodilators, produce NO in vivo and thus make up for a deficiency in the endogenous NO. By way of example, one might mention molsidomine or sodium nitroprussiate, which make it possible to prevent the phenomena of platelet adhesion and aggregation.

To make up for insufficient production of NO, there has even been a proposal for the administration of L-arginine or analogues of L-arginine, since L-arginine intervenes directly in the biosynthesis of nitrogen monoxide as a substrate of NO-synthase.

In view of the significant contribution made by nitrogen monoxide to the maintenance of a low pulmonary circulation pressure and the importance of the resultant local vasodilator effect, it has also been suggested that NO be directly administered by way of inhalation in the treatment of acute pulmonary arterial hypertension. The extensive research done along these lines demonstrated the therapeutic effectiveness of a gaseous mixture of nitrogen monoxide and inhaled nitrogen at doses between 1 and 20 ppm of NO on patients suffering acute respiratory disorders: in fact, a reduction of pulmonary arterial hypertension, possibly accompanied by an improvement of the ventilation-perfusion ratios due to an intrapulmonary shunt, was observed.

Surgical procedures involving laparoscopy are being practiced increasingly because, compared to conventional techniques involving open laparotomies, they make it possible to reduce not only the duration of hospitalization but also the scar formation time and, by the same token, post-operative pain.

However, although this technique of laparoscopy offers numerous advantages, it also entails one major inconvenience.

In effect, the technique of laparoscopy is usually accompanied by an insufflation of the abdomen (intra- or extra-peritoneal insulation) of a gas, such as $CO_2$, which insufflation causes an increase in the pressure being exerted inside the abdomen.

This increase in intra-abdominal pressure results in a decrease—harmful to the patient—of the blood flow of the abdominal organs, in particular, the kidneys and the intestines, and a disorder of the functions associated with these abdominal organs, such as diuresis and intestinal transit.

These disturbances are essentially due to a phenomenon of hypoperfusion of these organs, tied to the pressure increase due to insufflation; they are all the more harmful to the patient than the length of the procedure, in other words, the surgical operation, is important.

The object of this invention thus is to mitigate the above-described problems.

The invention thus relates to the use of a gaseous compound, containing nitrogen monoxide (NO) and carbon dioxide ($CO_2$), to produce a gaseous medication intended for the treatment or the prevention, by the intra-peritoneal route, of hypoperfusions of the abdominal organs.

By intra-abdominal route, we mean the intra-peritoneal or extra-peritoneal route.

The $NO/CO_2$ medication mixture of the invention is particularly suitable for the administration by intra-abdominal insufflation during a procedure involving laparoscopy or laparosurgery; the peritoneum here refers to the serous membrane that lines the abdominal cavity.

The gaseous medication of the invention is preferably made up of a single mixture of carbon dioxide and nitrogen monoxide; however, the addition of at least one gas chosen from the group made up of xenon, krypton, nitrogen protoxide and their mixtures, to said mixture of $CO_2$ and NO, can also be considered.

The concentration of NO in the gaseous mixture of NO+$CO_2$ is an effective concentration, preferably between 1 and 100 ppm. A concentration of less than 1 ppm is not desirable and a concentration of more than 100 ppm leads to a progressive disappearance of the therapeutic effect. The reasons for the low activity level observed in such concentrations are as yet unknown, but could be related to a local toxicity or possibly the saturation of the nitrogen monoxide receptors.

According to a preferred embodiment, the concentration of NO in the medication mixture is between 15 and 30 ppm.

The stability of the gaseous medication in this invention makes it possible to store it under pressure under conventional conditions in bottles made of steel or a light alloy on a base of aluminum.

To prevent any risk of contamination, bottles made of a light alloy on a base of aluminum are preferred. The preferred storage conditions that ensure stability in excess of 2 years are a temperature between 15 and 30° C., preferably between 20 and 25° C., and a pressure between 20 and 30 bar.

The compounds of the invention can be administered by means of intra-abdominal insufflation and, more particularly, by intra-peritoneal insufflation. To do that, we proceed in the known manner. After abdominal incision, the NO/$CO_2$ compound is insufflated into the abdominal cavity by means of a needle that is connected to an insufflator, such as the insufflator of the MP video type Medicam 900. Throughout the procedure, an internal pressure of between 10 and 20 mm Hg is maintained in the abdominal cavity. We note that the insulation of the mixture of $CO_2$ and nitrogen monoxide is neither described nor suggested in the literature. The vasodilating and platelet anti-aggregating activity of NO is particularly suitable for the treatment of side effects linked to a decline in vascular blood flow to the intra-abdominal organs during procedures involving laparoscopy.

The quantity of medication compound to be administered, however, depends on the age of the patient, the seriousness of the ailment from which he suffers, and the NO concentration of the injected gaseous compound.

Examples 1 to 2 below, illustrate the stability of the compounds of the invention, as well as their therapeutic usefulness.

EXAMPLE 1

Various mixtures of nitrogen monoxide and carbon dioxide were prepared and packaged in bottles of type B5, consisting of a light alloy, on a base of aluminum, sold through S. M. GERZAT, at a pressure of 24 bar. In these mixtures, the initial concentration of nitrogen monoxide was set at 20 ppm. The stability of the concentration in terms of NO was studied for 3 bottles kept at ambient temperature over a period of 16 months.

The value of the NO concentration was measured by an analyzer with chemiluminescence in the range of 0 to 100 ppm, calibrated before each measurement with the help of a standard NO/$N_2$ mixture at 90 ppm. The chemiluminescence analyzer employed is the TOPAZE 2020 made by COSMA.

At the end of a period of 16 months, no decomposition of the nitrogen monoxide in the NO/$CO_2$ mixtures, kept at ambient temperature, was detected. Indeed, the only fluctuations measured in the value of the concentration of NO remain below the precision of the analysis.

These results confirm the stability of the medication compounds of the invention.

EXAMPLE 2

This example is intended to demonstrate the effectiveness of the NO/$CO_2$ compound of the invention, administered by way of intra-peritoneal insufflation, in the struggle against the hypoperfusion of the abdominal organs and, in particular, the kidneys.

8 pigs, weighing approximately 25 to 30 kg, were anesthetized by intramuscular injection of ketamine (20 mg/kg) and mizadolam (0.1 mg/kg).

After intubation, the anesthesia was maintained by injection of fentanyl (5 µg/kg/h) and pancuronium (0.5 mg/kg/h), and by inhalation of a mixture of desflurane (5%), oxygen (50%) and nitrogen protoxide (45%).

We adjust the mechanical ventilation to maintain a partial remote-expiratory pressure of $CO_2$ which is less than 40 mm Hg.

Doppler® type detectors are implanted on the renal artery to measure the diameter of the arterial blood vessel and the speed of the blood so as to evaluate the average kidney blood flow.

In addition, a urinary probe is installed in the urethra to measure the urine flow.

The 8 pigs were divided into two groups of 4 pigs each. These 2 groups of 4 pigs underwent intra-peritoneal insufflation for 2 hours, and at a pressure of 15 mm Hg, consisting of the following:

gaseous $CO_2$ for group 1;

a gaseous mixture of NO/$CO_2$ (NO dose equal to 20 ppm) for group 2.

We observe a drop in the blood flow and the diuresis in the 2 groups of pigs, as of the start of insufflation. However, the drop is less for group 2 (NO/$CO_2$ insufflated). In effect, after insufflation, the blood and diuresis flow figures obtained for group 2 are 20% to 30% higher than those obtained for group 1.

The gaseous compound of NO/$CO_2$ of the invention makes it possible to effectively fight against the hypoperfusions of the abdominal organs when it is administered intra-abdominally, that is to say, extra-peritoneally or intra-peritoneally, thus, in particular, permitting an increase in the blood flow on the level of the abdominal organs.

We claim:

1. A method for the treatment or prevention of hypoperfusions of abdominal organs comprising administering to a patient in need thereof an effective amount of a gaseous medication comprising nitrogen monoxide and carbon dioxide; wherein said gaseous medication is administered by the intra-abdominal route.

2. The method of claim 1, wherein said gaseous medication further comprises at least one gas selected from the group consisting of xenon, krypton, nitrogen protoxide and a combination thereof.

3. The method of claim 1, wherein said nitrogen monoxide is present in said gaseous medication in a concentration of between 1 and 100 ppm.

4. The method of claim 1, wherein said nitrogen monoxide is present in said gaseous medication in a concentration between 15 and 30 ppm.

5. The method of claim 1, wherein said intra-abdominal route of administration is selected from the group consisting of the intra-peritoneal route and the extra-peritoneal route.

* * * * *